United States Patent [19]

Langer, Jr.

[11] Patent Number: 4,486,615

[45] Date of Patent: * Dec. 4, 1984

[54] PREPARATION OF LINEAR OLEFIN PRODUCTS

[75] Inventor: Arthur W. Langer, Jr., Watchung, N.J.

[73] Assignee: Exxon Research and Engineering Co., Florham Park, N.J.

[*] Notice: The portion of the term of this patent subsequent to Apr. 29, 1986 has been disclaimed.

[21] Appl. No.: 454,379

[22] Filed: Dec. 29, 1982

Related U.S. Application Data

[60] Continuation-in-part of Ser. No. 330,596, Dec. 14, 1981, Pat. No. 4,442,309, which is a continuation-in-part of Ser. No. 179,655, Aug. 20, 1980, Pat. No. 4,409,414, which is a continuation of Ser. No. 10,527, Feb. 9, 1979, abandoned, which is a division of Ser. No. 882,946, Mar. 2, 1978, Pat. No. 4,396,788, which is a continuation of Ser. No. 232,618, Mar. 7, 1972, abandoned, which is a continuation-in-part of Ser. No. 783,699, Dec. 13, 1968, Pat. No. 3,662,021, which is a continuation-in-part of Ser. No. 562,089, Jul. 1, 1966, abandoned, which is a continuation-in-part of Ser. No. 428,836, Jan. 28, 1965, abandoned, which is a continuation-in-part of Ser. No. 55,845, Sep. 8, 1960, Pat. No. 3,168,588.

[51] Int. Cl.$^3$ ............................................. C07C 2/22

[52] U.S. Cl. ....................................................... 585/523
[58] Field of Search ........................................ 585/523

[56] References Cited

U.S. PATENT DOCUMENTS 4,377,720 3/1983 Langer ................................. 585/523
4,396,788 8/1983 Langer ................................. 585/523

Primary Examiner—Paul M. Coughlan, Jr.
Attorney, Agent, or Firm—Richard E. Nanfeldt

[57] ABSTRACT

A process for preparing and controlling the $\overline{M}_n$ in the range of 70 to 700 of a reaction product comprising at least 90 mole % linear alpha olefins which includes polymerizing an ethylene containing gas in the presence of the reaction product of a Zirconium metal compound with $R_2AlX$, wherein R is an alkyl group having about 1 to about 20 carbon atoms, preferably 1 to 5, most preferably ethyl, and X is Cl or Br, in the presence of a diluent at a temperature of about 75° to 200° C. and an ethylene pressure above about 50 psia, wherein the mole ratio of ethylene to olefin reaction product is above 0.8 throughout the reaction, wherein the product olefin concentration is greater than 5 wt. % based on the diluent and reaction product, wherein the $\overline{M}_n$ of said reaction product is controlled by the molar ratio of said $R_2AlX/ZrCl_4$, said molar ratio being between 100:1 to 0.1:1.

8 Claims, No Drawings

PREPARATION OF LINEAR OLEFIN PRODUCTS

CROSS-REFERENCE TO RELATED APPLICATIONS

This application is a continuation-in-part of Ser. No. 330,596, filed 12/14/81, now U.S. Pat. No. 4,442,309, which is a continuation-in-part of Ser. No. 179,655, filed 8/20/80, now U.S. Pat. No. 4,409,414, which in turn is a continuation of Ser. No. 10,527, filed 2/9/79, now abandoned, which is a division of Ser. No. 882,946, filed 3/2/78, now U.S. Pat. No. 4,396,788, which is a continuation of Ser. No. 232,618, (now abandoned), filed 3/7/72, which is a continuation-in-part of Ser. No. 783,699, filed 12/13/68, now U.S. Pat. No. 3,662,021, which is a continuation-in-part of Ser. No. 562,089 (now abandoned), filed 7/1/66, which is a continuation-in-part of Ser. No. 428,836, filed 1/28/65, (now abandoned) which is a continuation-in-part of Ser. No. 55,845, filed 9/8/60, which is now U.S. Pat. No. 3,168,588.

FIELD OF THE INVENTION

This invention relates to an improved process for preparing linear olefins, particularly linear alpha olefins. More particularly, this invention relates to an improved process for polymerizing ethylene to obtain linear olefins having a number average molecular weight ranging from about 70 to 700.

Still more particularly, this invention relates to an improved process for polymerizing ethylene to obtain a product comprising at least 90 mole % linear alpha olefins having a number average molecular weight greater than about 200. Most particularly, this invention relates to an improved process for polymerizing ethylene to produce linear alpha olefins which comprises selectively terminating the polymerization reaction and inhibiting deleterious side reactions.

PRIOR ART

It has been shown in the prior art (U.S. Pat. Nos. 2,993,942 and 2,907,805) that hydrocarbon lubricating oils having a molecular weight in the range of 80 to 2000 could be prepared by polymerizing ethylene with controlled catalyst compositions, diluents and under controlled temperatures. The catalyst consisted of a transition metal halide and a halogenated aluminum alkyl compound. It has also been found that increased oil yields, catalyst reactivity, and improved molecular weight control could be obtained by the addition of a minor amount of a lower alkanol, as a catalyst modifier to the reaction system. Both the modified and unmodified systems described above resulted, under the conditions in the reaction, in the production of major portions of olefins other than linear alpha olefin products, particularly

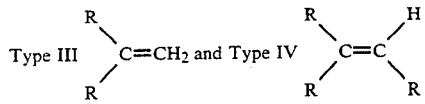

olefins.

It has now been discovered that the polymerization of ethylene under controlled conditions to produce linear olefins can be made selective for linear alpha olefins by terminating the reaction by the addition of an agent or agents to kill the activity of the catalyst and prevent deleterious side reactions. It has been found that the termination of the reaction by adding conventional catalyst killing agents, e.g., alcohol or water results in a product other than one comprising at least 90 mole % linear alpha olefins. The process of this invention required the termination of the ethylene polymerization reaction by the addition of specific agents under specific conditions. The ethylene polymerization reaction comprises a sequence of critical reaction variables comprising, inter alia, a mole ratio of ethylene to product, use of a particular catalyst, a particular cocatalyst to catalyst mole ratio, ethylene pressure, and product olefin concentration.

SUMMARY OF THE INVENTION

In accordance with this invention, therefore, an improved process for preparing linear olefins, particularly linear alpha olefins, is provided which comprises polymerizing ethylene or an ethylene containing gas in the presence of a catalyst comprising the reaction product of a Zr transition metal halide, with an aluminum alkyl compound such that the ultimate formula of the aluminum alkyl compound is $AlR_nX_{3-n}$, wherein n is less than 2, R is a hydrocarbyl radical, and X is a halogen, conducting the polymerization reaction in presence of a suitable diluent, at temperatures of about 75°–200° C. and ethylene pressures above about 50 psia, maintaining the mole ratio of ethylene to olefin reaction product above about 0.8 throughout the reaction, and killing catalyst activity after at least about 5 wt.%, based on diluent, of product olefin has formed by adding an agent or agents to kill the polymerization activity of the catalyst and preventing or inhibiting deleterious side reactions. In an embodiment of this invention a polymerization killing agent is added and another agent, designed to prevent or inhibit side reactions, e.g., isomerization, is added either before, after or simultaneously with the polymerization killing agent. In another embodiment of this invention a single agent can be added to the reaction mixture to accomplish both results, i.e., kill polymerization activity and inhibit deleterious side reactions. In yet another, and preferred embodiment, the polymerization killing agent is added to the reaction mixture prior to the removal of the ethylene from the reaction mixture. Generally, however, the agent or agents added to the reaction mixture are added under relatively critical conditions.

The reaction can be terminated either by removing the ethylene containing gas thereby stopping the polymerization; or, by adding the polymerization catalyst killing agent, thereby stopping the polymerization activity of the catalyst.

While not wishing to be bound by any particular theory, it is believed that the catalysts employed herein as ethylene polymerization catalysts tend also to promote the copolymerization of the product olefins formed by the reaction. Now since the object of this invention is to produce and maintain a product comprising at least 90 mole % linear olefins, it is obvious that copolymerization of the reaction product will lead to increased formation of branched products at the expense of linear products. Consequently, the reaction must be terminated at a suitable point where an economically feasible product yield has been obtained but prior to the occurrence of copolymerization to the extent that it reduces product purity to a level below about 90 mole % linear olefins. While generally conventional polymerization killing agents can be added to the reaction mixture to terminate the polymerization activity of the catalyst, e.g., water, alcohols, acids, etc., such agents tend to protonate the catalyst and turn it into a strongly acidic Friedel-Crafts catalyst. A Friedel-Crafts catalyst in the reaction mixture, however, promotes isomerizations, alkylations, carbonium ion polymerizations, etc., which are deleterious in that such side reactions reduce the linearity of the reaction product. Consequently, it is often-times necessary to add an additional agent, i.e., a base, to the reaction mixture to neutralize the Friedel-Crafts activity of the catalyst.

Generally, catalyst activity may be killed before or after the ethylene is removed from the reaction mixture. When the catalytic activity is killed after ethylene removal the polymerization killing agent must be added within about one minute after ethylene removal. This is a critical variable in the preservation of the linear olefin reaction product. Thus, as previously mentioned, the polymerization catalyst also promotes copolymerization of the product olefin. However, copolymerization is inhibited due to the relatively high mole ratio of ethylene to produce olefin maintained throughout the reaction. (This ratio is maintained by the high ethylene pressure, i.e., above about 50 psia ethylene, in the reaction mixture which promotes ethylene polymerization activity rather than copolymerization). When the ethylene has been removed the selectivity to ethylene polymerization is lost and copolymerization will be promoted. In order to prevent copolymerization from destroying the linear product it is critical that the polymerization activity of the catalyst be killed within about one minute of ethylene removal. After killing the polymerization activity with a conventional agent, the Friedel-Crafts activity must be neutralized, also within a critical period. Thus, side reactions due to the presence of an acidic catalyst can also destroy the linear reaction product. The base, or neutralizing agent, must then be added within about on minute after the polymerization activity is killed.

Of course, this invention contemplates the addition of the base prior to the addition of the polymerization killing agent. Nevertheless, polymerization activity must be killed within about one minute of ethylene removal. Thus, if the base is added one minute after ethylene removal, the polymerization killing agent must be added simultaneously. However, the base may be added within about two minutes after ethylene removal if the polymerization killing agent is first added about one minute after ethylene removal.

The foregoing critical relationships hold where the reaction is terminated at ambient temperatures, i.e., room temperatures of about 18°-25° C., and above. It will be obvious to those skilled in the art that if the temperature of the reaction mixture is reduced, i.e., taken below room temperature, after the polymerization activity is killed, addition of the base can be delayed somewhat. Of course, the lower the temperature of the reaction mixture, the longer base addition can be delayed. Using the very general rule that reaction rate doubles or halves with each 10° C. change in temperature, a rough guide can be established and the period during which the base must be added (to prevent undue isomerizations, alkylations, etc.) can be readily found by simple experimentation.

Thus, the general rule is that the polymerization activity of the catalyst be killed within about one minute after termination of the reaction. It is preferred, however, to add the polymerization killing agent prior to the termination of the reaction, i.e., before the ethylene is flashed off, a point which is obviously within the general period just stated. This procedure eliminates observance of the critical period when the reaction is terminated prior to killing polymerization activity. Additionally, the critical period for base addition is also obviated since the reaction mixture will be auto refrigerated due to flashing the ethylene, e.g., the temperature can be reduced to below $-10°$ C. by auto refrigeration. Furthermore, at reduced temperatures the catalyst can be washed out thereby eliminating the acid function and obviating the need for a neutralizing agent.

Some typical polymerization killing agents are water, alcohols, both mono- and poly hydroxylic, cyclic and acyclic, aliphatic and aromatic; carboxylic acids, phenols, etc. The organic compounds which can be used are those having from 1 to 15 carbon atoms, the lower carbon number inexpensive compounds being preferred. Thus alcohols and acids having from 1 to 8 carbons are preferred, with 1 to 4 carbons being most preferred. Examples of the most preferred killing agents include water, methanol, ethanol, isopropanol, t-butanol, and ethylene glycol.

Bases that can be employed to neutralize Friedel-Crafts activity can be any base that will effectively neutralize this acid function. Generally, such bases can be broadly characterized as Lewis bases. Such materials which can be used in the practice of this invention include caustics such as alkali metal and alkaline earth metal hydroxides and carbonates, ammonium hydroxide and quaternary ammonium bases and organic bases such as organic nitrogen compounds, e.g., ammonia, amines and cyclic nitrogen bases, and ethers, etc. As specific example, there can be named lithium hydroxide, sodium hydroxide, potassium carbonate, magnesium hydroxide, calcium carbonate, tetramethylammonium hydroxide, $C_1$–$C_{10}$ aliphatic amines, e.g., ethylamine, methyl-amine and aniline p-toluidine, ammonia, heterocyclic nitrogen compounds, e.g., pyridine, and tetrahydrofuran. These bases may be used alone, in mixtures or dissolved in solvents such as water, alcohols, glycols, etc. The preferred bases are sodium hydroxide or ammonia dissolved in water or alcohols. Although larger amounts may be used, it is desirable to use 0.5 to 2 moles of base per atom of halogen in the catalyst, preferably about stoichiometric amounts. It is obvious that a base such as sodium hydroxide dissolved in water or alcohols serves to kill polymerization activity simultaneously with neutralization. Lewis bases kill polymerization activity by complexing more strongly than alpha olefins with the transition metal site. On the other hand, protonic agents kill polymerization activity by destroying the metal-carbon bonds of the catalyst. Thus, a base is needed in addition to the protonic agents to neutralize the Friedel-Crafts activity of the catalyst residues, whereas a Lewis base such as triethylamine inactivates both types of catalyst activity.

The catalyst which can be used is a complex reaction product which is obtained by partially reacting a reducible transition metal halide of Group IVB to VIB or VIII with an aluminum alkyl compound such that the ultimate formula of the aluminum alkyl compound is $AlR_nX_{3-n}$, wherein n is less than 2, R is alkyl, cycloalkyl or aralkyl, preferably containing 1 to 20 carbon atoms, for example, methyl, ethyl, isobutyl, cyclohexyl, benzyl, etc., and X is Cl or Br or I. While most transition metal halides are suitable components of the catalyst complex, when the desired product is the branched chain olefins of the prior art, it has been found that compounds such as VCl$_4$ and FeCl$_3$ are unsuitable for the preparation of linear alpha olefins. The preferred transition metal catalyst components is a Zr metal compound having a valency of 4, and may be represented by the formula: ZrX$_a$A$_b$, wherein a=3 or 4, b-0 or 1 and a+b=3 or 4, X=Cl or Br and A is Cl or Br or an anion derived from a protonic compound such as an alcohol (R'OH) or a carboxylic acid (R'COOH). The R' of the protonic compound may be an alkyl, aryl, aralkyl or cycloalkyl group. The ZrX$_a$A$_b$ component may be made in situ by reacting ZrX$_4$ with the protonic compound. Thus, the preferred transition metal component of this invention may be selected from the group ZrX$_4$, ZrX$_3$OR' and ZrX$_3$OOCR'. Typical examples of such compounds are ZrCl$_4$, ZrBr$_4$, ZrX$_3$OC$_2$H$_5$, and ZrX$_3$OOCCH$_3$.

The transition metal component may also be a halide, an alkoxide or a carboxylate derivative of tetravalent zirconium or hafnium having the general formulas MX$_n$(OR)$_{4-n}$ and MX$_n$(OOCR')$_{4-n}$, where M=Zr or Hf, X-Cl or Br, n=0 to 4 and R' may be an alkyl, aryl, aralkyl or cycloalkyl group. When these components are reacted with the excess aluminum alkyl chlorides, exchange or ligands takes place involving halide, alkyl, alkoxide and carboxylate groups. In addition to exchange of aluminum alkyl groups with transition metal ligands, the aluminum halide groups can also exchange with alkoxy and carboxyl groups on the transition metal compound. These compounds may also be made in situ by reacting the more readily available MX$_4$ with R'OH or R'COOH. The alcohols may be unsaturated as in the case where they are the enol forms of carbonyl compounds such as acetyl acetone. Typical examples include ZrCl$_4$, ZrBr$_4$, ZrCl(OEt)$_3$, ZrCl$_2$(OC$_{10}$H$_{21}$)$_2$, ZrBr$_3$oBu, Zr(OPr)$_4$, Zr(OBu)$_4$, ZrCl$_2$(O$\phi$)$_2$, ZrCl$_2$(OOCC$_9$H$_{19}$)$_2$, ZrCl(OOC$\phi$)$_3$, ZrCl$_3$OOCCH$_3$, ZrCl$_2$ glycoxide, Zr acetyl acetonate, ZrCl$_3$(O-cyclohexyl), HfCl$_4$, HfBr$_4$, Hf(OBu)$_4$, etc., in which the hydroxy groups are not attached to adjacent carbon atoms are also useful. Especially preferred and desirable are: tertiary butanol, secondary butanol, iso- or n-butanol, and isopropanol. These alkanols are utilized in a minor amount, i.e. so that the ratio of ROH/R (based on aluminum alkyl) after alkylation or reduction of the transition metal is not greater than 0.5.

It has been surprisingly found that when one employs a catalyst system comprising an R$_2$AlX wherein R is an alkyl group having about 1 to 20 carbon atoms, preferably 1 to 5, most preferably ethyl, and X is Cl or Br, preferably Cl; and ZrCl$_4$ for the polymerization of ethylene, the M$_n$ of the formed polyethylene increases as the molar ratio of R$_2$AlX/ZrCl$_4$ decreases, over the range 100:1 to 0.1:1. Ratios below 1:1 are preferred for obtaining high selectivity to wax and less than 0.5:1 is most preferred. Ratios between 50:1 and 1:1 are preferred for making high purity liquid alpha olefins.

Ethylene is unique in the instant invention in that other olefins do not respond to give linear alpha olefins. Therefore, it is desirable to use essentially pure ethylene or mixtures of ethylene with inert gases as the feed for the process of this invention. Ethylene feeds containing minor amounts of other olefins may be used provided that the extent of copolymerization does not decrease product linearity below 90%.

Polymerization diluent is not a critical feature of this invention. The useable diluents are aromatic hydrocarbon and haloaromatic solvents as well as aliphatics and naphthenics. Less preferred solvents are halogenated aliphatic compounds which, while capable of being employed in the process of preparing linear alpha olefins, require the utilization of higher pressures to achieve average molecular weights of the same order as the preferred solvents. The preferred diluents include halogenated aromatics such as chlorobenzene, dichlorobenzene, chlorotoluene, etc., aromatics such as benzene, toluene, xylene tetrahydronaphthalene, etc., aliphatics such as pentane, heptane, iso-octane, etc., a naphthenes such as cyclohexane, methylcyclohexane, decahydronaphthalene, etc. The suitable halogenated aliphatic diluents include methyl chloride, ethyl chloride, dichloromethane, etc. Mixtures of these diluents may be used. Also, mixtures of the above types with aliphatic or naphthenic solvents may be used. The diluent or diluent mixture may be used to control the product molecular weight distribution to obtain maximum selectivity to the desired olefin products.

Lewis bases may be added to the catalyst to increase activity and $\overline{M}_n$ and also to suppress polyethylene formation. The amount of Lewis base is critical and is related to the amount of EtAlCl$_2$ in the system after alkylation of the ZrCl$_4$ by Et$_2$AlCl. Any amounts in excess of the EtAlCl$_2$ act as strong catalyst poisons, whereas amounts equal to or less than the EtAlCl$_2$ increase both activity and $\overline{M}_n$. Order of addition does not appear to be very important as good results are obtained when the Lewis base is added to the cocatalyst, to the ZrCl$_4$ or to the catalyst mixture before or in the presence of ethylene. Any Lewis base which complexes EtAlCl$_2$ in the presence of alkylated zirconium chloride may be used. Typical examples include tertiary amines, secondary amines, ethers, phosphine oxides, alkyl and aryl phosphates, sulfoxides, etc. Tertiary amines, such as triethylamine are preferred.

The prior art obtained highly branched olefins (60%) when using the closely related catalyst and diluent systems at pressures of 7 to 30 psig., e.g., British Pat. No. 974,577. Ethylene pressures above 50 psia are essential for making linear olefins in high selectivities. Although some variations are permitted depending upon the catalyst composition, diluent and temperature, the preferred pressures are above about 80 to 100 psia in order to produce commercially attractive yields (at least above 5 weight % and preferably above 10 weight % olefins in the reactor effluent) of linear alpha olefins having a purity greater than about 90 mole %. The most preferred range is above 100 psia ethylene pressure. At very high ethylene pressures the process may become uneconomical because of the equipment requirements and ethylene recycle. Nevertheless, higher pressures tend to increase the selectivity of the reaction to linear alpha olefins.

The ratio of moles of ethylene to the moles of products throughout the reaction and insured by the ethylene pressures referred to above, must be above about 0.8 in order to effect the selective synthesis of linear olefins from ethylene and inhibit copolymerization effects. The preferred ratio of ethylene to products is above about 2.0. The upper limit of the mole ratio of ethylene to product is not critical. The mole ratio of ethylene to product must be above 0.8 to the product formed contains more than 10% branched chain olefins at product concentrations required to obtain commercially attractive yields.

The catalyst of this invention enables the process for making linear alpha olefins to be carried out at temperatures of about 75° to about 200° C., preferably between about 100° C. and about 180° C. The selection of a particular temperature will permit control of the number average molecular weight of the total product. With zirconium and hafnium catalysts, temperatures as high as about 200° C. can be used without making excessive amounts of polyethylene. However, the high temperatures cause product isomerization and require higher ethylene pressures to prevent copolymerization which make them less attractive. The preferred temperatures to obtain high purity linear alpha olefins with zirconium tetrachloride catalysts are between about 75° to about 200° C. and, more preferably, between about 100° to about 180° C. and most preferably about 120° to 150° C., to obtain total product $\overline{M}_n > 200$.

Reaction times are not particularly critical when operating under the preferred conditions and they will normally be in the range of 0.1 to 5 hours to obtain product concentrations greater than 5% by weight in the diluent. The process may be carried out in batch or continuous operation. However, high product purity and high concentration are achieved most easily in batch reactions or in continuous systems operating under essentially plug flow conditions. A reactor may consist of a long pipe through which the diluent and catalyst flow with ethylene being introduced at many points along the pipe to maintain the desired ethylene concentration. In such a system monomer concentration need not be constant but may be controlled differently in different sections of the reactor to achieve the best balance of activity, molecular weight and product purity. Stirred tank reactors may be operated in series to approach plug flow.

After the catalyst has been effectively neutralized, the residues may be removed from the products in any conventional way, such as washing with water or aqueous caustic, adsorption, ion exchange resins, etc. If the catalyst has been neutralized according to this invention, the products may be distilled directly from the catalyst residues without decreasing product purity. However, it is preferred to remove the residues before distillation in order to minimize deposits in the distillation towers.

Based on the teachings of this invention to destroy both polymerization and Friedel-Crafts activity to permit isolation of greater than 95% pure linear alpha olefins, it is clearly within the scope of the invention to accomplish the same results by alternatives such as rapid solvent extraction or solid adsorption techniques, particularly if these are used before all of the ethylene has been flashed. However, such techniques are generally less effective than the preferred neutralization procedure.

The following examples are submitted in order to more particularly point out applicant's invention but are not to be constructed as limitations upon the scope of the instant invention as described in the appended claims.

EXAMPLE 1

A series of runs were made to determine the effect of ethylene pressure on product linearity. All were carried out at $-20°$ C. using 500 ml of either chlorobenzene or xylene diluent. THe proportions of catalyst components were maintained constant, although total catalyst concentration was varied by a factor of four. The TiCl$_4$ in 400 ml diluent was added to the reactor under dry nitrogen and cooled at $-20°$ C. The t-butyl alcohol and AlEt$_2$Cl were mixed 5 minutes in 100 ml diluent before adding the AlEtCl$_2$. The latter was added to the reactor and the total mixture allowed to react 15 minutes at $-20°$ C. High purity ethylene was obtained by passing commercial C.P. ethylene over copper oxide at 205° C. to remove oxygen and then through 3A molecular sieves to remove water. It was stored in a one-gallon reservoir at 1000 psig. After the catalyst pretreatment, the reactor contents were subjected to high speed stirring. Ethylene was added as necessary to maintain pressure and the temperature was kept at $-20°$ C. by circulating coolant through coils around the reactor.

The results are summarized in Table I. After killing the catalyst with about 25 to 50 ml methanol containing NaOH, the product was water-washed twice and dried over K$_2$CO$_3$. The products were analyzed quantitatively for olefin types by infrared, and the split between linear and branched products was determined by quantitative gas chromatography on a sample of total reactor product. Using a four-foot column of silicone gum rubber and temperature programming, it was possible to obtain the yield of each product up to C$_{36}$H$_{72}$. Product linearity is expressed as mole % in the C$_{12-20}$ fraction. It was compared on the C$_{12-20}$ cuts because this was the most accurate analysis considering volatility losses from C$_{4-10}$ and G. C. resolution of the branched and linear olefins about C$_{20}$. The linearity of the total product is much higher than that shown for the C$_{12-20}$ fraction because in all pressure runs the C$_{4-10}$ fraction is essentially 100% linear, and it is a major portion of the total product.

As shown in Table I, the selectivity to linear alpha olefins increases sharply above about 50 psia and becomes greater than 90% above about 100 psia. At still higher ethylene pressures, selectivity rapidly approaches 100% in the C$_{12-20}$ fraction. Excellent results were obtained with either chlorobenzene or xylene diluent. In addition to the effect on olefin linearity, ethylene pressure may be used together with catalyst, composition, solvent polarity and polymerization temperature to control the product molecular weight. As shown in Table I for chlorobenzene diluent, the number average molecular weight increased from 98.8 at atmospheric pressure to 147 at 500 psia.

TABLE I

| Run | mmoles (a) A/B/C/D | Diluent | Hours | psia C$_2$H$_4$ | g. Product/ g/TiCl$_4$/Hr. | (c) $\overline{M}_n$ | % Linear Olefins in C$_{12-20}$ |
|---|---|---|---|---|---|---|---|
| 3 | 12/12/2/2 | C$_6$H$_5$Cl | 1 | 15 (b) | 45 | 98.8 | 67 |
| 4 | 12/12/2/2 | C$_6$H$_5$Cl | 1 | 55 | 95 | 100.5 | 70 |
| 5 | 12/12/2/2 | Xylene | 1 | 140 | 105 | 121.4 | 98 |
| 6 | 6/6/1/1 | C$_6$H$_5$Cl | 1 | 165 | 147 | 112.6 | 97 |
| 7 | 3/3/0.5/0.5 | C$_6$H$_5$Cl | 2 | 250 | 74 | 121.3 | 99 |

TABLE I-continued

| Run | mmoles (a) A/B/C/D | Diluent | Hours | psia $C_2H_4$ | g. Product/ g/$TiCl_4$/Hr. | (c) $M_n$ | % Linear Olefins in $C_{12-20}$ |
|---|---|---|---|---|---|---|---|
| 8 | 12/12/2/2 | Xylene | 1 | 250 | 97 | 140.0 | 100 |
| 9 | 12/12/2/2 | $C_6H_5Cl$ | 0.5 | 500 | 126 | 147.0 | 100 |

A   B   C   D
(a) Catalyst: $AlEt_2Cl/AlEtCl_2/TiCl_4$/t-BuOH.
(b) Gaseous ethylene bubbled continuously through diluent at atmospheric pressure.
(c) Number average molecular weight of total olefin product.

EXAMPLE 2

A catalyst solution containing 1.5 mmoles $AlEt_2Cl$, 3.0 mmoles $AlEtCl_2$ and 3.0 mmoles $TiCl_4$ in 250 ml xylene was pretreated 30 minutes at 15° C., cooled to 0° C. and ethylene added rapidly. Polymerization was carried out two hours at 0° C. and 520 psia ethylene pressure. Samples of the total reactor product were taken hourly and analyzed as in Example 1.

In taking the reactor samples, the ethylene is allowed to flash off at atmospheric pressure, thereby refrigerating the sample. The first hour sample (10 ml) was allowed to stand 15 minutes before killing the catalyst with 1 ml of 1M NaOH in methanol. The second hour sample (18 ml) was pressured from the reactor directly into a vessel containing the 1 ml of 1M NaOH in order to kill the catalyst immediately. The amount of NaOH was taken to be approximately equivalent to the chloride content of the catalyst in the sample.

Alkylation took place so extensively in the first hour sample that it was impossible to do the usual analysis. Product concentration was estimated to be about 30 to about 40 weight %. No linear alpha olefins were indicated by infrared analysis. The product was prediminantly alkylated xylene.

The second hour sample was 96.9% linear alpha olefins despite the fact that product concentration was much higher (53.6 weight %). By analogy with all other experiments, the first hour sample should have had the highest linearity; in this case, an estimated 98 to 99% if the catalyst had been destroyed immediately after flashing ethylene.

This example illustrates that high purity olefins can only be obtained by rapid destruction of the catalyst activity after flashing ethylene.

EXAMPLE 3

A catalyst solution was prepared by reacting 12 mmoles $AlEt_2Cl$ and 2 mmoles t-butanol in 95 ml chlorobenzene for 5 minutes, then adding 12 mmoles $AlEtCl_2$. 400 ml chlorobenzene containing 2 mmoles $TiCl_4$ was charged to the reactor, cooled to −20° C., the aluminum alkyl solution was added, and the catalyst was pretreated 15 minutes at −20° C. Ethylene was charged to 155 psia and polymerization was continued one hour at 150 to 160 psia and −20° C.

The total reactor product was flashed into 100 ml methanol without any base present. After filtering off 4.8 grams wax, the filtrate was water-washed, dried over $K_2CO_3$ and distilled using a 15 plate Oldershaw column at 20/1 reflux ratio. Infrared analysis of the $C_4$-$C_8$ cut gave only 80% linear alpha olefins and 20% internal olefins (Type II-trans). Since some Type II-cis olefins would have been produced simultaneously by isomerization, the linear alpha olefin purity was considerably less than 80%.

Experiments in which the products were flashed into methanol plus NaOH gave over 98% pure linear alpha olefins. In the infrared analyses of these samples, the Type II-trans absorption at 10.3 was barely discernible.

This example illustrates that rapid quenching of the catalyst polymerization activity is not sufficient to obtain high purity alpha olefins. In the absence of a base, double bond isomerization occurs to produce the less desirable internal olefins. It shows that it is critical to destroy the Friedel-Crafts activity of the catalyst as well as the polymerization activity. Besides double bond isomerization, residual catalyst Friedel-Crafts activity could also cause alkylation and cationic polymerizations which would further decrease the alpha olefin purity.

With high polymers any residual polymerization or Friedel-Crafts activity has a negligible effect, if any, on product properties. In a process for making linear alpha olefins, however, it is critical to destroy or neutralize both types of catalyst activity.

EXAMPLE 4

Following the procedure of Example 3 but terminating the polymerization with 10 ml methanol plus 10 ml $6HNH_4OH$ prevented isomerization and preserved the alpha olefin purity.

EXAMPLE 5

A series of runs were made to determine the effect of quenching various catalyst compositions. The reaction conditions are set forth in Table II. In each run the reaction was quenched with a mixture of methanol and NaOH. It is to be seen from Table II that the instant process resulted in a highly linear product.

TABLE II

| Run | 1 | 2 | 3 | 4 |
|---|---|---|---|---|
| $AlEtCl_2$, mmoles | 5 | 2 | 5 | 0.5 |
| $AlCl_3$, mmoles | 0 | 0 | 0.2 | 0 |
| $TiCl_4$, mmoles | 1 | 1 | 0.05 | 1 |
| Solvent | Xylene | Xylene | $C_6H_5Cl$ | $C_6H_5Cl$ |
| ml | 125 | 125 | 250 | 250 |
| Pretreat, °C./min. | 25/60 | 50/30 | 50/30 | 50/30 |
| Al/Ti Mole Ratio | 5 | 2 | 104 | 0.5 |
| Et/Al Ratio (a) | 0.8 | 0.5 | 0.95 | 0 |
| Polymerization | | | | |
| Temp. °C. | 15 | 50 | 50 | 50 |
| $C_2H_4$, psia | 400 | 400 | 400 | 400 |
| Time, Hrs. | 1 | 1 | 3 | 0.5 |
| Results | | | | |
| Yield, g (b) | 132 | 92 | 23 | 51 |
| Linearity, Mole % (c) | 91.5 | 91.2 | 95.2 | 94.3 |
| $M_n$ | 113 | 128 | 114 | 116 |

(a) Assuming mon-alkylation of TiCl
(b) Excluding 10-20% losses during work-up
(c) Determined on $C_{12-20}$ fraction

EXAMPLE 6

A catalyst solution was prepared by mixing 0.1 mmole $ZrCl_4$ and 0.2 mmole phenol in 40 ml chlorobenzene for 5 minutes at 50° C., then adding 0.4 mmole Al$_2$Et$_3$Cl$_3$ and pretreating 15 minutes at 60° C. The solution was rinsed into a pressure catatlyst bomb with an additional 10 ml chlorobenzene and pressured with ethylene into the reactor containing 150 ml chlorobenzene and 890 psia C$_2$H$_4$ at 70° C. The temperature and pressure were immediately raised to 75° C. and 1015 psia ethylene pressure and maintained for 30 minutes.

G. C. samples were flashed into 1M NaOH in methanol, n-heptane was added and the solutions were washed with aqueous K$_2$CO$_3$ solution, separated and dried over solid K$_2$CO$_3$. Analyses were carried out using a 15 ft. column of SE-30 (2% on Choromsorb G) and temperature programming to 340° C. The yield of olefins between C$_4$ and about C$_{40}$ after 15 minutes was 48 g and after 30 minutes it was 90 g. Linear alpha olefin purity in the C$_{12-20}$ fraction was 99+%. Extraction of the wax with boiling n-heptane less than 0.1 g insoluble product.

EXAMPLE 7

The procedure of Example 6 was followed except that n-butanol was used in place of phenol and it was mixed with either the ZrCl$_4$ or the ethyl aluminum sesquichloride for 5 minutes at 25° C. before adding the second catalyst component and pretreating. In Runs 1 and 2 of Table III, no alcohol was added. Variations in catalyst composition, catalyst pretreatment and reaction conditions are given in the Table.

TABLE III

| Run | mmoles A/B/C/D (a) | Diluent | Catalyst Pretreat, °C./min. | Oligomerization Temp. °C. | Time, Min. | g. Olefins/ g. Catalyst (b) | $\overline{M}_n$ | % Linear Olefins in C$_{12}$-C$_{20}$ |
|---|---|---|---|---|---|---|---|---|
| 1 | 0.4/0.4/0.1/0 | C$_6$H$_5$Cl | 60/30 | 75 | 30 | 473 | 93 | 99+ |
| 2 | 0.2/0.2/0.05/0 | C$_6$H$_5$Cl | 80/30 | 100 | 30 | 1295 | 111 | 98 |
| 3 | 0.4/0.4/0.1/0.4 | C$_6$H$_5$Cl | 50/15 | 75 | 60 | 1090 | 148 | 98 |
| 4 | 0.4/0.4/0.1/0.4 (c) | C$_6$H$_5$Cl | 90/15 | 75 | 30 | 385 | 158 | 99+ |
| 5 | 0.2/0.2/0.05/0.2 | C$_6$H$_5$Cl | 50/15 | 125 | 30 | 1275 | 154 | 95 |
| 6 | 0.4/0.4/0.1/0.4 | n-C$_7$H$_{16}$ | 50/15 | 75 | 30 | 262 | 140 | 99+ |

(a) Catalyst AlEt$_2$Cl/AlEtCl$_2$/ZrCl$_4$/n-BuOH.
(b) Excluding the n-butanol.
(c) The n-butanol was reacted first with the Al$_2$Et$_3$Cl$_3$ rather than with ZrCl$_4$.

In all runs catalyst activity was excellent. The purity of the linear alpha olefins in the C$_{12-20}$ fraction ranged from 95% to nearly 100%. Total product molecular weight ranged from 93 to 158, illustrating the control of product distribution. At $\overline{M}_n$=93, selectivity to C$_{4-10}$ is 76.8% whereas at the higher molecular weights ($\overline{M}_n$=140–158), one obtains the highest selectivity to C$_{12-18}$ detergent range olefins.

No significant amount of polyethylene was obtained in any of these experiments.

EXAMPLE 8

The procedure of Example 7 was followed except that zirconium propoxide and zirconium dipropoxy dichloride were performed rather than being made in situ by reacting ZrCl$_4$ with propanol. Variations in catalyst composition, pretreatment and reaction conditions are summarized in Table IV.

TABLE IV

| Run | mmoles A/B/C (a) | Diluent | Catalyst Pretreat, °C./min. | Temp. °C. | Time, Min. | g. Olefins/ g. Catalyst | $\overline{M}_n$ | % Linear Olefins in C$_{12}$-C$_{20}$ |
|---|---|---|---|---|---|---|---|---|
| 1 | 0.2/0/0.2 | n-C$_7$H$_{16}$ | 50/15 | 50 | 30 | 0 | — | — |
| 2 | 0.2/0.6/0.2 | n-C$_7$H$_{16}$ | 80/5 | 50 | 30 | 572 | 188 | 99+ |
| 3 | 0.9/0.9/2 | C$_6$H$_5$Cl | 50/15 | 75–170 (c) | 15 | 652 | 141 | 95 |
| 4 | 0/0.8/0.2 (b) | C$_6$H$_5$Cl | 60/15 | 50 | 30 | 417 | 172 | 99+ |

(a) A/B/C = AlEt$_2$Cl/AlEtCl$_2$/Zr(OPr)$_4$
(b) ZrCl$_2$(OPr)$_2$ was used in place of the tetraalkoxide.
(c) Lost temperature control allowed temperature to rise to about 170° C. momentarily. Most of the run was at 80° C.

Run 1 used equimolar amounts of AlEt$_2$Cl and Zr(OPr)$_4$ and was completely inactive, whereas Run 2 used 8:1 Al:Zr mole ratio and was very active. This illustrates that preformed zirconium alkoxides require an excess of aluminum alkyl halide just as was found for the in situ preparation using the alcohols. In either case, the ratio of ROH (or RO groups on the Group IVB metal)/R (based on aluminum alkyl) after alkylation of the transition metal is preferably less than about 0.5.

Run 3 produced a small amount of polyethylene, presumably because of the excessively high reaction temperature reached momentarily. Based on this result and those in Example 7, the maximum desirable reaction temperature is about 150° C. for the zirconium catalysts. Product purity drops at the higher temperatures due to copolymerization and isomerization of the alpha olefins so that the preferred reaction temperature for making high purity linear alpha olefins is below 125° C., most preferably below about 75° C.

Run 4 shows that preformed zirconium alkoxy chlorides are as effective as those formed in situ from the alcohols. Having demonstrated the utility of ZrX$_4$, ZrX$_2$(OR)$_2$ and Zr(OR)$_4$, it is clear that other mixed alkoxy halides will also be useful (for example, ZrCl$_3$OR, ZrCl(OR)$_3$, etc.).

EXAMPLE 9

The procedure of Example 6 was followed except that 0.2 mmole neodecanoic acid (Enjay Chemical Co.) was used in place of phenol. Neodecanoic acid is a mixture of C$_{10}$ acids having three alkyl substituents on the alpha carbon (R$_1$R$_2$R$_3$CCOOH). The mole ratio of 2 acids per ZrCl$_4$ yields the dichlorodicarboxylate, ZrCl$_2$(OOCR)$_2$.

After 30 minutes at 75° C. and 1015 psia ethylene pressure, the olefin yield was 68 g and the purity was 99+%.

EXAMPLE 10

The procedure of Example 6 was followed except that 0.4 mmole acetylacetone was used in place of phenol and the ZrCl$_4$-acetylacetone reaction product was pretreated 15 minutes at 50° C. with 0.8 mmole Al$_2$Et$_3$Cl$_3$. The alcohol form (enol) of acetylacetone reacts with the catalyst in the same manner as saturated alcohols. The product (91 g) was 99% pure linear alpha olefins.

EXAMPLE 11

The procedure of Example 6 was followed except that 0.2 mmole benzoic acid was used in place of phenol, yielding a clear, colorless solution with the 0.1 mmole ZrCl$_4$. Addition of 0.6 mmole Al$_2$Et$_3$Cl$_3$ and pretreatment for 15 minutes at 50° C. produced a cler, very light yellow solution. After 30 minutes oligomerization at 75° C. and 1015 psia ethylene pressure, a high yield of high purity linear alphs olefins was obtained.

EXAMPLE 12

A slurry of ZrCl$_4$, DEAC, 5 g n-C$_{11}$H$_{24}$ internal standard and 500 ml n-heptane was charged at about 50° C. to the reactor under nitrogen, the reactor gas phase was evacuated briefly, the reactor temperature was increased to 20° C. below the final run temperature, ethylene was pressured rapidly to reach 7 MPa to run temperature in less than about 2 minutes. Ethylene was fed continuously to maintain 7 MPa.

The effect of DEAC/ZrCl$_4$ ratio on product $\overline{M}_n$ was studied at two run temperatures (120° C. and 130° C.).

TABLE V

| Run | DEAC mmol | ZrCl$_4$ mmol | Al/Zr | Temp. °C. | Time, Min. | Rate g/g ZrCl$_4$/hr | $\overline{M}_n$ | % Purity |
|---|---|---|---|---|---|---|---|---|
| A | 0.40 | 0.10 | 4.0 | 120 | 15 | 32,000 | 150 | 95.5 |
| B | 0.10 | 0.10 | 1.0 | 120 | 15 | 18,000 | 196 | 98.5 |
| C | 0.10 | 0.20 | 0.5 | 120 | 15 | 17,000 | 215 | 96.3 |
| D | 0.04 | 0.16 | 0.25 | 120 | 15 | 11,600 | 248 | 99.6 |
| E | 0.08 | 0.08 | 1.0 | 130 | 15 | 12,600 | 174 | 99.3 |
| F | 0.06 | 0.24 | 0.25 | 130 | 15 | 6,100 | 224 | 99.9 |

Surprisingly, $\overline{M}_n$ increased with decreasing Al/Zr ratio, especially below 1/1. This is particularly attractive for making olefin wax because the selectivity to wax increases rapidly at total product molecular weights above 200.

EXAMPLE 13

The procedure of Example 12 was followed except that high ratios of DEAC/ZrCl$_4$ were used and EtAlCl$_2$ (EADC) was also present in Runs G and H.

EADC appears to have little effect on $\overline{M}_n$ and acts mainly to lower activity. This has utility in controlling the reaction rate and polymerization conditions with these extraordinarily active catalysts. At Al/Zr ratios of 22 to 50, the product $\overline{M}_n$ was in the range of 78 to 107 and represents a continuation of the trend toward lower $\overline{M}_n$ with increasing Al/Zr, shown in Table V. Therefore, $\overline{M}_n$ can be readily controlled over the range of about 70 to 300 by using Al/Zr ratios between about 100:1 and 0.1:1.

TABLE VI

| Run | EADC mmole | DEAC mmole | ZrCl$_4$ mmole | Al/Zr | n-C ml. | Temp °C. | Time, min. | Rate g/g ZrCl$_4$/hr. | $\overline{M}_n$ | % Purity |
|---|---|---|---|---|---|---|---|---|---|---|
| G | 1.0 | 1.5 | 0.05 | 50 | 350 | 120 | 20 | 6200 | 78 | 98.4 |
| H | 0.1 | 1.0 | 0.05 | 22 | 350 | 120 | 15 | 36200 | 107 | 96.0 |
| I | 0 | 1.0 | 0.04 | 25 | 500 | 130 | 30 | 9300 | 83 | 97.0 |

The effect of Al/Zr ratio is directly opposite to that taught by Ziegler for DEAC/TiCl$_4$ ratio in which polyethylene molecular weight increases sharply with increasing ratio. (Belgium 540,459 (2/9/56); see Raff and Doak, Crystalline Olefin Polymers I, Interscience 1965, p. 372.) Clearly, we are dealing with different catalyst species (tetravalent Zr) rather than the reduced transition metal species in typical Ziegler catalyts. Thus one cannot extrapolate the broad disclosures of reduced Ziegler-type catalysts for polyethylene to the alkylated but unreduced tetravalent catalysts for ethylene oligomerization to alpha olefins.

EXAMPLE 14

The procedure of Example 12 was followed except that triethylamine (Et$_3$N) was added to the catalyst components or the polymerization under a variety of conditions and molar amounts as shown in Table VII.

When the Et$_3$N was added to a polymerization in progress, the activity increased dramatically as shown by the incremental rates (Runs J, K, P and Q). The molecular weight of the incremental product also increased substantially, especially in the high molecular weight runs. These improved results were obtained regardless of the time at which Et$_3$N was added (Run O at the start, Run P at 5 minutes, Run Q at 15 minutes, Run J at 50 and 65 minutes, and Run K at 75 minutes).

Similar results were obtained when the Et$_3$N was first complexed to the ZrCl$_4$ (Run L) or to the DEAC (Runs M and N). Also, these improvements were obtained over a wide range of Al/Zr ratios.

The limitation on the amount of Lewis base which can be added is shown in Runs Q and J. In Run Q, the catalyst activity was killed when the molar amount of Et$_3$N exceeded the molar amount of aluminum alkyl cocatalyst. In Run J, the activity was high in spite of a high ratio of Et$_3$N to ZrCl$_4$ because a larger amount of cocatalyst was present. Thus, the molar amount of Lewis base must be equal to or less than the amount of aluminum alkyl cocatalyst, especially the amount of EtAlCl$_2$ in the system after alkylation of the ZrCl$_4$.

TABLE VII

| Run | mmoles EADC | mmoles DEAC | mmoles ZrCl₄ | Et₃N | Et₃N Added | Run Total | °C. | Rate × 10⁻³ Ave | Rate × 10⁻³ Δ | % Purity | $\overline{M}_n$ Ave | $\overline{M}_n$ Δ |
|---|---|---|---|---|---|---|---|---|---|---|---|---|
| J | 1.0 | 2.5 | 0.05 | — | — | 50 | 120 | 8.2 | — | 94.3 | 80 | — |
|   |   |   |   | +0.5 | 50 | 65 | 120 | 11.2 | 21.2 | 92.6 | 83 | 87 |
|   |   |   |   | +0.4 | 65 | 80 | 120 | 14.0 | 26.1 | 91.1 | 83 | 83 |
| K | 0.1 | 0.05 | 0.1 | — | — | 30 | 120 | 2.1 | — | 99.1 | 142 | — |
|   |   |   |   | +0.1 | 75 | 80 | >120 | — | >30 | — | — | — |
| L | 0.1 | 0.5 | 0.1 · Et₃N | — | — | 30 | 120 | 20.6 | — | 97.8 | 202 | — |
| M⁽ᵃ⁾ | — | 0.05 · Et₃N | 0.1 | — | — | 30 | 120 | 11.0 | — | 99.1 | 218 | — |
| N | — | 0.05 · Et₃N | 0.2 | — | — | 15 | 130 | 6.1 | — | 99.7 | 235 | — |
| O | — | 0.05 | 0.1 | +0.05 | 0 | 15 | 120 | 17.9 | — | 99.1 | 254 | — |
| P | — | 0.1 | 0.1 | — | — | 5 | 120 | 14.9 | — | 99.4 | 186 | — |
|   |   |   |   | +0.1 | 5 | 30 | 120 | 19.1 | 19.3 | 97.4 | 196 | 198 |
| Q | — | 0.05 | 0.1 | — | — | 15 | 120 | 5.0 | — | 99.5 | 205 | — |
|   |   |   |   | +0.05 | 15 | 30 | 120 | 5.8 | 6.7 | 99.5 | 250 | 298 |
|   |   |   |   | +0.05 | 30 | 40 | 120 | Dead | 0 | — | — | — |

⁽ᵃ⁾Catalyst components premixed in 20 ml. toluene before adding to heptane diluent.

What is claimed is:

1. A process for preparing and controlling the $\overline{M}_n$ in the range of 70 to 700 of a reaction product comprising at least 90 mole % linear alpha olefins which comprises polymerizing an ethylene containing gas in the presence of the reaction product of a $ZrCl_4$ with $R_2AlX$, wherein R is an alkyl group having about 1 to about 20 carbon atoms and X is Cl or Br, in the presence of a diluent at a temperature of about 75° to 200° C. and an ethylene pressure above about 50 psia, wherein the mole ratio of ethylene to olefin reaction product is above 0.8 throughout the reaction wherein the product olefin concentration is greater than 5 wt.% based on the diluent and reaction product, wherein the $\overline{M}_n$ of said reaction product is controlled by the molar ratio of said $R_2AlX/ZrCl_4$, said molar ratio being between 100:1 to 0.1:1.

2. A wax process according to claim 1, wherein said molar ratio is between 1:1 to 0.1:1.

3. A process according to claim 1, wherein said $R_2AlX$ is $R_2AlCl$.

4. A process according to claim 1 wherein said temperature is about 100° to 180° C.

5. A process according to claim 1 wherein said temperature is about 120° to about 150° C.

6. A liquid olefin process according to claim 1, wherein said molar ratio is between about 50:1 to 1:1.

7. A process according to claim 2 or 6 wherein said ethylene pressure is at least 1000 psig.

8. A process according to claim 1 in which $RAlX_2$ is added to moderate catalyst activity.

* * * * *